(12) United States Patent
Asprey et al.

(10) Patent No.: US 11,285,335 B2
(45) Date of Patent: Mar. 29, 2022

(54) PHOTO-THERAPEUTIC METHOD AND APPARATUS

(71) Applicant: Biohacked, Inc., Kent, WA (US)

(72) Inventors: David Asprey, Cobble Hill (CA); Timothy K. Brodesser, Auburn, WA (US); Haiping Zeng, Guangzhou (CN)

(73) Assignee: Biohacked, Inc., Kent, WA (US)

( * ) Notice: Subject to any disclaimer, the term of this patent is extended or adjusted under 35 U.S.C. 154(b) by 81 days.

(21) Appl. No.: 16/154,673

(22) Filed: Oct. 8, 2018

(65) Prior Publication Data

US 2020/0108268 A1    Apr. 9, 2020

(51) Int. Cl.
*A61N 5/06* (2006.01)

(52) U.S. Cl.
CPC .... *A61N 5/0616* (2013.01); *A61N 2005/0626* (2013.01); *A61N 2005/0652* (2013.01); *A61N 2005/0659* (2013.01); *A61N 2005/0663* (2013.01)

(58) Field of Classification Search
CPC ................................................. A61N 5/0616
See application file for complete search history.

(56) References Cited

U.S. PATENT DOCUMENTS

| | | | |
|---|---|---|---|
| 4,932,934 A | 6/1990 | Dougherty et al. | |
| 5,071,416 A | 12/1991 | Heller et al. | |
| 5,800,479 A | 9/1998 | Thiberg | |
| 6,666,878 B2 | 12/2003 | Carlgren | |
| 6,860,896 B2 | 3/2005 | Leber et al. | |
| 7,201,765 B2 | 4/2007 | McDaniel | |
| 7,887,533 B2 | 2/2011 | Barolet et al. | |
| 8,852,254 B2 | 10/2014 | Moscovici | |
| 8,858,607 B1 | 10/2014 | Jones | |
| 8,938,295 B2 | 1/2015 | Baird et al. | |
| 8,945,196 B2 | 2/2015 | Huttemann et al. | |
| 9,017,391 B2 | 4/2015 | McDaniel | |
| 9,132,279 B2 | 9/2015 | Roersma et al. | |
| D740,985 S | 10/2015 | Dooley | |
| D778,456 S | 2/2017 | Knaus | |
| D794,813 S | 8/2017 | Zsolcsak | |
| D831,839 S | 10/2018 | Pelletier | |
| 2002/0183811 A1 | 12/2002 | Irwin | |
| 2003/0009158 A1 | 1/2003 | Perricone | |
| 2004/0068305 A1 | 4/2004 | Bansal | |
| 2004/0122492 A1 | 6/2004 | Harth et al. | |
| 2004/0232359 A1 | 11/2004 | Fiset | |
| 2005/0004631 A1 | 1/2005 | Benedict | |

(Continued)

OTHER PUBLICATIONS

2 TinEye search results from examination in U.S. Appl. No. 29/668,795, dated Jul. 25, 2019, in 3 pages.

(Continued)

*Primary Examiner* — Rex R Holmes
*Assistant Examiner* — Jennifer L Ghand
(74) *Attorney, Agent, or Firm* — Knobbe, Martens, Olson & Bear, LLP

(57) ABSTRACT

A wavelength specific photo-modulation treatment device and method are disclosed which provide specific wavelength colors from a group of four different electromagnet colors arranged in a repeating scalable matrix array. The device includes a control system connected to the array for driving the devices in two different modes and three different color combinations.

11 Claims, 7 Drawing Sheets

(56) References Cited

U.S. PATENT DOCUMENTS

| | | | |
|---|---|---|---|
| 2005/0177093 A1* | 8/2005 | Barry | A61N 5/0613 604/20 |
| 2006/0212025 A1* | 9/2006 | McDaniel | A61N 5/0617 606/9 |
| 2006/0229689 A1* | 10/2006 | Ferguson | A61N 5/0616 607/88 |
| 2006/0241363 A1 | 10/2006 | Al-Ali et al. | |
| 2006/0259102 A1 | 11/2006 | Slatkine | |
| 2006/0276860 A1 | 12/2006 | Ferren et al. | |
| 2007/0038269 A1 | 2/2007 | Whitehurst | |
| 2007/0208289 A1 | 9/2007 | Walther | |
| 2007/0233208 A1* | 10/2007 | Kurtz | A61N 5/0613 607/88 |
| 2008/0065176 A1* | 3/2008 | Zhang | A61N 5/0616 607/88 |
| 2008/0103560 A1* | 5/2008 | Powell | A61N 5/0616 607/88 |
| 2008/0269849 A1 | 10/2008 | Lewis | |
| 2009/0177125 A1 | 7/2009 | Pilcher et al. | |
| 2009/0312822 A1 | 12/2009 | Besner | |
| 2010/0049177 A1* | 2/2010 | Boone, III | A61H 9/0057 606/9 |
| 2012/0035690 A1* | 2/2012 | Turtzo | A61F 7/00 607/90 |
| 2012/0130455 A1* | 5/2012 | Baird | A61N 5/0617 607/90 |
| 2013/0289679 A1* | 10/2013 | Eckhouse | A61N 1/06 607/102 |
| 2014/0288351 A1* | 9/2014 | Jones | A61N 5/0624 600/9 |
| 2015/0025599 A1 | 1/2015 | Bornstein | |
| 2015/0176777 A1* | 6/2015 | Hikmet | F21V 9/32 362/84 |
| 2015/0182758 A1* | 7/2015 | Ajiki | A61N 5/0616 607/88 |
| 2016/0121108 A1* | 5/2016 | Kondo | A61N 1/328 601/2 |
| 2016/0175609 A1* | 6/2016 | Dye | A61N 5/0616 607/90 |
| 2016/0250498 A1 | 9/2016 | Bean et al. | |
| 2016/0279437 A1 | 9/2016 | Park | |
| 2016/0367833 A1 | 12/2016 | Salinas | |
| 2017/0225012 A1* | 8/2017 | Dotson | A61B 3/1241 |
| 2017/0246475 A1 | 8/2017 | Marchese | |
| 2017/0312542 A1 | 11/2017 | Palaniswamy | |
| 2018/0207446 A1 | 7/2018 | Jones | |
| 2018/0236259 A1 | 8/2018 | Nelson | |
| 2018/0360665 A1 | 12/2018 | Melone | |
| 2019/0111278 A1 | 4/2019 | Tapper | |

OTHER PUBLICATIONS

9 TinEye search results from examination in U.S. Appl. No. 29/668,795, dated Jul. 25, 2019, in 8 pages.

Alster et al., "Improvement of postfractional laser erythema with light-emitting diode photomodulation," Dermatol. Surg., 35(5):813-5, May 2009, PMID: 19397672, DOI: 10.1111/j.1524-4725.2009.01137.x, Abstract only.

Avci et al., "Low-level laser (light) therapy (LLLT) in skin: stimulating, healing, restoring," Semin Cutan Med Surg., Author manuscript, available in PMC, Aug. 8, 2014, 25 pages.

Barolet et al., "Infrared and Skin: Friend or Foe," J Photochem Photobiol B., Author manuscript, available in PMC Feb. 2017, PMCID: PMC4745411, NIHMSID: NIHMS746721, PMID: 26745730, 19 pages.

Chaves et al., "Effects of low-power light therapy on wound healing: LASER v LED," An Bras Dermatol. 2014;89(4):616-23, DOI: http://dx.doi.org/10.1590/abd1806-4841.20142519.

De Lima et al., "Use alone or in Combination of Red and Infrared Laser in Skin Wounds," J Lasers Med Sci., Spring 2014; 5(2): 51-57, PMCID: PMC4291816, PMID: 25653799.

Ferraresi et al., "Low-level laser (light) therapy (LLLT) on muscle tissue: performance, fatigue and repair benefited by the power of light," Photonics and Lasers in Medicine 1, No. 4 (Nov. 2012): 267-286.

Goldberg et al., "Combined 633-nm and 830-nm led treatment of photoaging skin," J Drugs Dermatol., Sep. 2006; 5(8):748-53, Abstract only.

Hamblin et al., "Mechanisms of low level light therapy," Proc. of SPIE, vol. 6140, 614001, (2006), 13 pages, doi: 10.1117/12.646294.

Hashmi et al., "Effect of Pulsing in Low-Level Light Therapy," Lasers Surg Med., Author manuscript, available in PMC Aug. 1, 2011, 25 pages.

Iurshin et al., "Etiopathogenetic basis for using magnetolaser therapy in the complex treatment of male infertility," Urologiia, Mar.-Apr. 2003; (2):23-5, PMID: 12811920, Abstract only.

Piccolo et al., "Unconventional Use of Intense Pulsed Light," Clinical Study, Hindawi Publishing Corporation, BioMed Research International, vol. 2014, Article ID 618206, 10 pages, http://dx.doi.org/10.1155/2014/618206.

Al Rashoud et al., "Efficacy of low-level laser therapy applied at acupuncture points in knee osteoarthritis: a randomised double-blind comparative trial," Physiotherapy, vol. 100, Issue 3, pp. 242-248, Sep. 2014, DOI: https://doi.org/10.1016/j.physio.2013.09.007, Abstract only.

Sawhney et al., "Low Level Laser (Light) Therapy (LLLT) for Cosmetic Medicine and Dermatology," retrieved from the Internet on Dec. 17, 2018, at http://photobiology.info/Sawhney.html, 42 pages.

Sivapathasuntharam et al., "Aging retinal function is improved by near infrared light (670 nm) that is associated with corrected mitochondrial decline," Neurobiol Aging, Apr. 2017, 52: 66-70, PMCID: PMC5364001, PMID: 28129566, doi: 10.1016/j.neurobiolaging.2017.01.001, 9 pages.

Vatansever et al., "Far infrared radiation (FIR): its biological effects and medical applications", Photonics Laser Med. Nov. 1, 2012; 4:255-266.

Lohr et al., "Far Red/Near Infrared Light Treatment Promotes Femoral Artery Collateralization in the Ischemic Hindlimb", J Mol Cell Cardiol., Sep. 2013, 62:36-42.

Geneva, Ivayla, "Photobiomodulation for the treatment of retinal diseases: a review", Int J Ophthalmol, vol. 9, No. 1, Jan. 18, 2016, pp. 145-152.

Yoshimura et al., Abstract of "Photobiomodulation reduces abdominal adipose tissue inflammatory infiltrate of diet-induced obese and hyperglycemic mice", J Biophotonics, Dec. 2016, 9(11-12):1255-1262, https://pubmed.ncbi.nlm.nih.gov/27635634, in 1 page.

Jonasson et al., Abstract of "Effects of low-level laser therapy and platelet concentrate on bone repair: Histological, histomorphometric, immunohistochemical, and radiographic study", J Craniomaxillofac Surg., Nov. 2017, 45(11):1846-1853, https://pubmed.ncbi.nlm.nih.gov/28935484, in 2 pages.

Opel et al., "Light-emitting Diodes A Brief Review and Clinical Experience", The Journal of Clinical and Aesthetic Dermatology, Jun. 2015, vol. 8, No. 6, pp. 36-44.

Mota et al., "Efficacy of phototherapy to treat facial ageing when using a red versus an amber LED: a protocol for a randomised controlled trial", BMJ Open, 2018, 8:e021419, in 7 pages.

Mitrofanis et al., "Does photobiomodulation influence ageing?", Aging 2018, vol. 10, No. 9, Sep. 15, 2018, www.aging-us.com, pp. 2224-2225.

Inoué et al., Abstract of "Biological activities caused by far-infrared radiation", Int J Biometeorol, Oct. 1989, 33(3):145-50, in 1 page.

\* cited by examiner

PHOTO-THERAPEUTIC METHOD AND APPARATUS

TECHNICAL FIELD

The invention relates to photo-therapeutic treatment of human conditions. More specifically, the invention relates to methods and apparatus for photo therapeutic treatment of the human dermis and sub-dermal layers using specific wavelengths of electromagnetic radiation.

BACKGROUND

Photo-therapeutic treatment of human maladies has been known since the time of the ancient Greeks. In modern history, tuberculosis sanatoriums often included solar insolation as treatment for that malady. The development of wavelength specific light sources, and particularly the solid-state light emitting diodes have enabled manufacturers to provide economically viable photo-therapeutic devices using specific wavelengths and frequencies of visible and near-visible electromagnetic radiation to treat specific maladies. The understanding of correlations between specific frequencies/wavelengths of photo-therapies and specific maladies has been largely empirical. Although the basic formulas for relating electromagnetic frequencies and wavelengths to specific energy densities is well known by the product of frequency and plank's constant (E=hf), or the product of plank's constant and the speed of light divided by the wavelength. Increases in frequency (and thus decrease in wavelength) while resulting in higher energy densities does not necessarily translate into deeper penetration of those wavelengths into the human dermis, or absorption of those wavelengths by biological agents in the human body. Primarily, this is due to scattering as the light enters the dermis, and whether or not the particular biological agent has physical size which is resonant with a specific frequency associated with that wavelength. As a consequence, extensive research has been done by third parties related to specific wavelengths of visible and near-visible light which impact human biological functions through photo-biomodulation (hereinafter "PBM"). For example, recent National Institute of Health Studies for Eye Health have shown that near-infrared radiation (670 nm) advantageously repairs damaged retinal function by correcting mitochondrial decline and stimulating Inosine tri-phosphate (ITP) production in the Krebs cycle. See Sivapathasuntharam et al., "Aging Retinal Function is Improved by Near Infrared Light (670 nm) that is Associated with Corrected Mitochondrial Decline" Journal of Neurobiological Aging, April, 2017; 52:66-70. Huttemann et al. disclose in U.S. Pat. No. 8,945,196, the disclosure which is incorporated herein by reference that light therapy for ischemic events (oxygen starvation) can be improved by exposing the effected tissues to wavelengths in the range of 730 nm to 770 nm, infrared radiation in the range of 850 nm to 890 nm and invisible radiation in the range of 930 nm to 970 nm. Paradoxically, Huttemann et al. contend that such irradiation prevents rapid re-profusion injury by suppressing reactive oxygen species which exacerbates cell death and such therapies are beneficial after myocardial infraction and cerebral ischemia. Thus, rather than stimulating a biological function, Huttemann et al. discovered empirically that suppression of biological function can be advantageous.

Baird et al. disclosed in U.S. Pat. No. 8,938,295, (the disclosure of which is incorporated herein by reference), that a hand-held direct contact device having light emitting diodes operating at the following wavelengths, 605 nm, 630 nm, 660 nm, and 940 nm are beneficial for treating various forms of dermatitis such as Rosacea. Baird et al believe that such wavelengths stimulate fibroblasts to generate collagen. Baird et al overdrive the LEDs into thermal heating temperatures of 97 degrees to 106 degrees Fahrenheit to open up the pores of the dermis. Jones teaches in U.S. Pat. No. 8,858,607 (the disclosure of which is incorporated herein by reference), that it may be necessary to provide convection cooling of LED lights to prevent overheating. McDaniel teaches in U.S. Pat. No. 9,017,391 (the disclosure of which is incorporated herein by reference and assigned to L'Oréal) that a variety of different wavelengths in the visible and near-visible electromagnetic spectrum have different absorption rates for human fibroblast absorption which may be effective for treating a variety of human maladies. Photosensitizing drugs may also be used to concentrate light absorption and energy transfer for the treatment of tumors (See U.S. Pat. No. 4,932,934 to Dougherty et al.) and further, light therapy may be coordinated with circadian rhythms and ultradian cycles to improve keratin growth. See published application 2015/0025599 to Bornstein.

As should be apparent from the above review of the relevant prior art, the state of the art with respect to photo-therapeutic treatment of various human conditions, including preferred frequencies and wavelengths is largely empirical, without sound theoretical basis and somewhat contradictory. Thus, a need exists for a photo-therapeutic method and apparatus which specifically targets various human maladies in specific wavelengths. A further need exists for an apparatus and method which limits such photo-therapeutic treatments in both duration and intensity. Further, a need exists for a photo-therapeutic treatment method and apparatus which avoids application of various dangerous frequencies and wavelengths and is cognizant of contrary indicated modalities.

DETAILED DESCRIPTION

Figure 1:
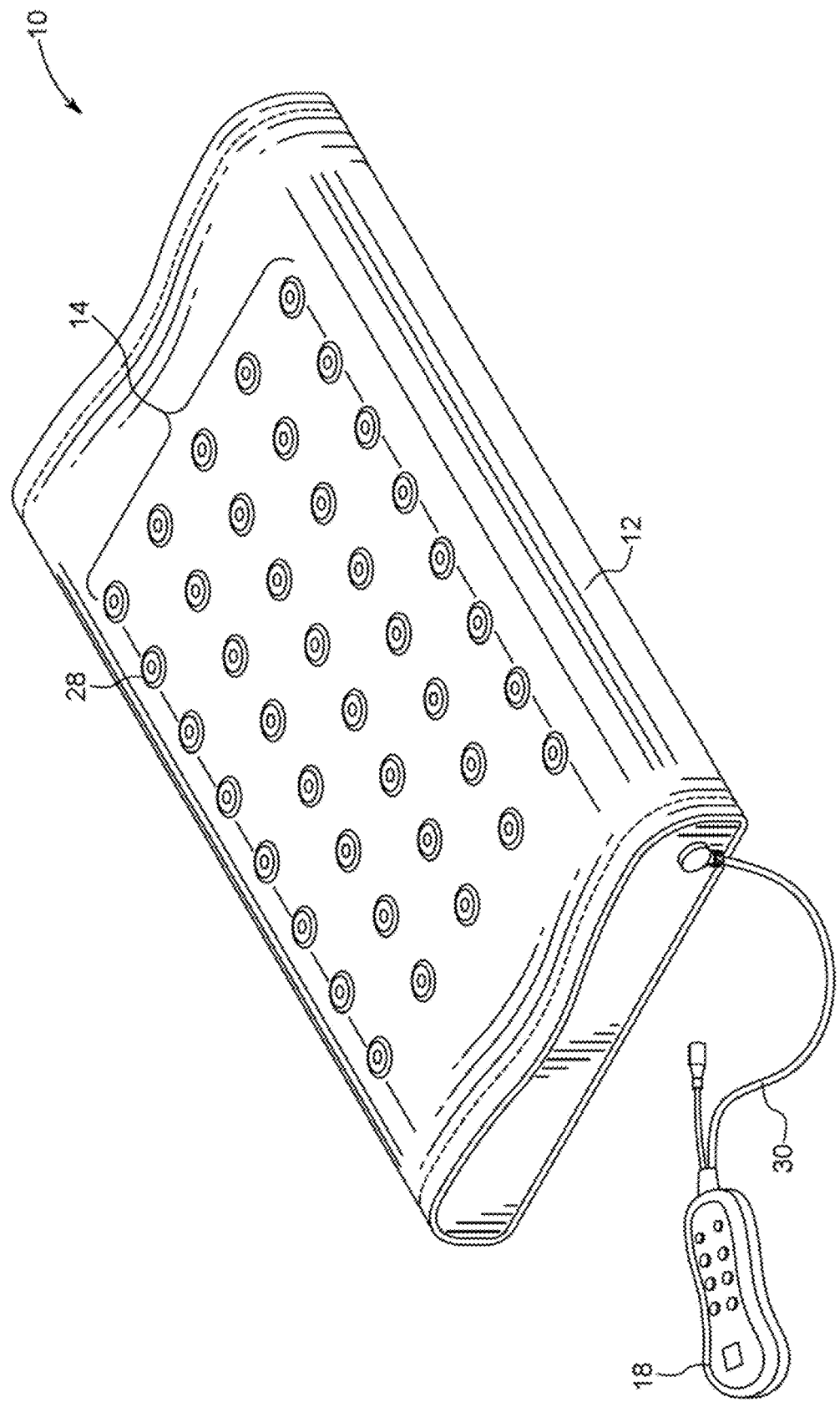
FIG. 1 is an environmental view of a wavelength specific photo-modulation dermal treatment device encased in a soft pillow including a remote control.

The present disclosure provides for a photo-therapeutic apparatus and method which specifically targets various human maladies in specific wavelengths. Certain embodiments also limit such photo-therapeutic treatments in both time and intensity and avoid application of various dangerous frequencies and wavelengths and is cognizant of contra indicated maladies.

The example photo-therapeutic apparatus and method is achieved by providing a wavelength specific photo-modulation dermal treatment method and device utilizing a plurality of light emitting devices, selected from a color group of four different electromagnetic colors arranged in a repeating, scalable matrix array having a preselected matrix pattern. In an example embodiment, a control system is provided for driving the devices in the array in two difference modes and three different color combinations. A machine interface is operably connected to the control system for allowing an operator to select the modes and color combinations for treatment of a specific malady. To effect treatment, human dermis is exposed to the device according to the selected mode and selected color combinations correlating to treatment of the specific malady. A maximum treatment time may be programmed into the treatment device to prevent overexposure.

In some example embodiments, the first mode drives all of the devices of a select color continuously, and in a second mode all the devices of a selected color or colors are driven at a duty cycle. The wavelengths of the light emitting devices preferably correspond to yellow, short red, red and near infrared electromagnetic radiation and preferably have wavelengths corresponding to approximately 580 nm, 630 nm, 660 nm and 850 nm, respectively. The wavelength 810 is avoided.

In other example embodiments, the matrix pattern consists of a first row of devices having a repeating left to right sequence of a first, second and third color; a second row of devices having a repeating left to right sequence of the colors decremented with respect to the colors of the first row; a third row of devices having devices all of the same fourth color; and a fourth row of devices having a repeating left to right sequence of the first, second, and third colors decremented with respect to the colors of the second row, together all defining the matrix pattern. In some embodiments, the matrix array of devices is housed in a soft pillow enclosure which may be foldable and rollable. In other embodiments, the machine interface is a remote controller which is operably connected to the control system either by hard wire, radio frequency or by other means of communication.

A wavelength specific, photo-modulation treatment device in accordance with the principles described above is generally indicated at reference numeral 10 in the various Figures of the attached drawings wherein numbered elements in the figures correspond to like numbered elements herein. The treatment device includes a housing 12 including a light emitting device array generally indicated by the reference numeral 14. The housing encloses a controller 16 generally shown in FIG. 3 for driving the light emitting device array. The treatment device further includes a remote control 18 operably connected to the controller 16 to provide a man machine interface for selecting various colors and modes of the array 14. The treatment device also includes a power supply 20 as best seen in FIG. 2 for energizing the controller 16 which drives the array 14.

The treatment device 10 is a photo-modulation therapy device that emits energy for use in dermatology, muscle relaxation and tissue recovery. The device delivers optimal visible and near-visible electromagnetic radiation associated with near-infrared, deep red, red and yellow/amber wavelengths which are believed to react with cellular mitochondria to increase adenosine triphosphate (ATP) production. In turn, increased ATP production leads to faster production of collagen, vascular structures, DNA, RNA and other materials that are essential to the body's healing process. These wavelengths enhance blood circulation, reduce wrinkles and fine lines, increase muscle recovery and decrease redness/irritation. There are no user settings or adjustments other than the first button 22, second button 24, and third button 26 associated with the remote control 18 best seen in FIG. 3. Maximum treatment time for safe utilization of the treatment device is automatically fixed by the controller 16 as will be described in further detail herein below. As used herein, "light emitting device" include narrow spectrum resistive bulbs, lasers, masers, light emitting diodes, florescent bulbs, high intensity discharge bulbs and other means of generating narrow bandwidth electromagnetic radiation yet to be reduced to practice. As used herein a preferred wavelength or frequency means an electromagnet emission having a fundamental frequency (f0) or wavelength (λ) and a bandwidth of less than approximately 20 nm. In the embodiments shown in FIGS. 1 and 2, the light emitting devices are light emitting diodes which are generally available with a specific wavelength and power distribution properties which will be described further herein below. With respect to the first embodiment shown in FIG. 1, the matrix array 14 includes a plurality of light emitting diodes 28 in a five row by eight column matrix array. The foldable alternate embodiment shown in FIG. 2 includes an elongated flexible housing 12' including a matrix array 14' of LEDs 28 in a 26 row by 8 column matrix array. In one embodiment, the remote control communicates with the controller 16 contained in the housings 12, 12' by a cable 30 or by wireless radio frequency transmission as will be described further herein below. As best seen in FIG. 3 the controller 16 includes a micro-controller 32 operatively connected to a first channel driver 34 which energizes only the LEDs 28 associated with the color yellow and a second channel driver 36 associated with driving only the LEDs 28 associated with the color red (deep red, red and near infrared). The controller 16 can be provided with a receiving antenna 38 if wireless operation with the remote control 18 is desired.

Figure 4:
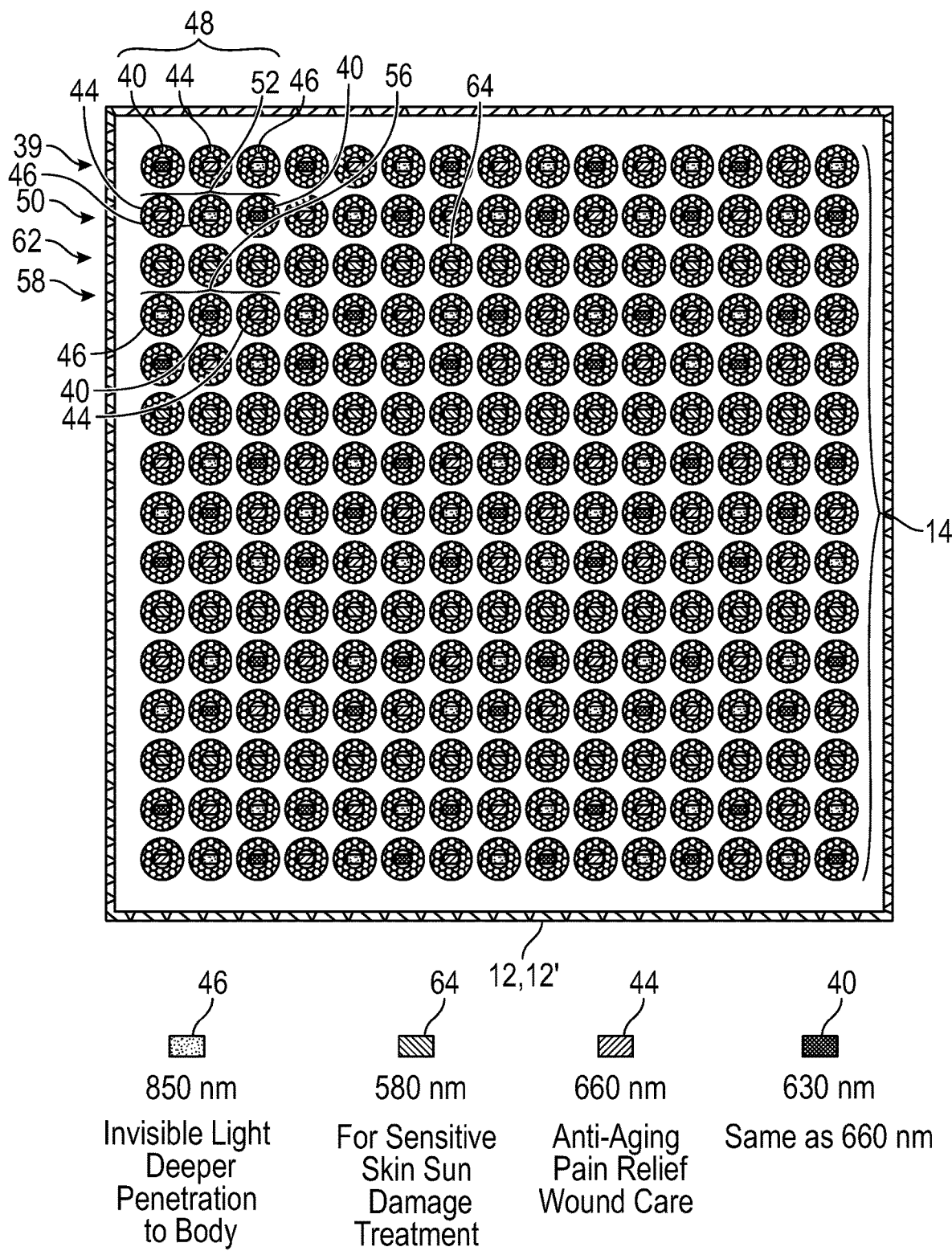
FIG. 4 is a schematic representation of a matrix array of light emitting devices having a preselected matrix pattern.

FIG. 4 is a schematic representation of a representative light emitting device array 14 consisting of a plurality of the LED's 28. The LED's are arranged in a repeating pattern of rows and columns which is advantageously scalable using the driving circuitry 34, 36 under operation of the controller 16 merely by repeating the sequence of LED colors as described herein. Array 14 includes a first row of LED's generally indicated at reference numeral 39. Specifically, beginning at the upper left-hand corner of the array 14, in the first row and first column (Cartesian coordinate 1,1) a deep or short red LED 40 having a wavelength of approximately 630 nm is provided. Moving to the right, a red LED 44 having a wavelength of approximately 660 nm is provided occupying the Cartesian coordinate, (1,2). Next, an invisible light infrared LED 46 is provided at Cartesian coordinate (1,3). That three LED sequence (indicated at reference numeral 48) repeats moving to the right four times making for a total five sequences 48 of the short red, red and infrared LED's 40, 44, and 46. The next row moving down generally indicated by the reference numeral 50 includes a second sequence 52 of LED's including red LED 44, near-infrared LED, 46 and short red LED 40. Those LED's occupy the Cartesian coordinates (2,1); (2,2); and (2,3) respectively, and that sequence 52 is repeated to the right in the second row 50 four times as well making for a total of five sets of second sequence LED's 52 in the second row 50. Those of ordinary skill in the art will note that the second sequence 52 is identical to the first sequence 48 except that the LED's are decremented by one color. Skipping to a fourth row 58, a third sequence of LED's 56 includes an infrared LED 46 occupying Cartesian coordinate (3,1); a short red LED 40 occupying Cartesian coordinate (4,2); and a red LED 44 occupying Cartesian coordinate (4,3) forming a third sequence 56. That sequence is repeated four times to the right as with first row 39 and second row 15. Again, those of ordinary skill in the art will note that the third sequence 56 is identical to the second sequence 52, except that the colors have been decremented by one color. A skipped third row 62 consists all of a single color of LED, preferably a yellow LED 64 having a preferred wavelength of approximately 580 nm. As will be described in further details herein below, the yellow LED's 64 are only used in the preferred method during daylight hours so as to not disturb the diurnal sleep cycle. As is apparent from review of FIG. 4, the first, second and third sequence of LED's 48, 52 and 56 along with three yellow LED's occupying Cartesian coordinates (3,1); (3,2); and (3,3) together comprise a four row by three column sub array which is repeated moving to the right and repeated moving down to create a scalable array of any size which can be driven by appropriately selected first and second channel drivers 34, 36 resulting in a matrix array having various dimensions which will be applicable for full body treatments such as that shown in FIG. 2 or treatments of the scalp or other smaller areas of the body such as with the embodiment shown in FIG. 1.

Figure 2:
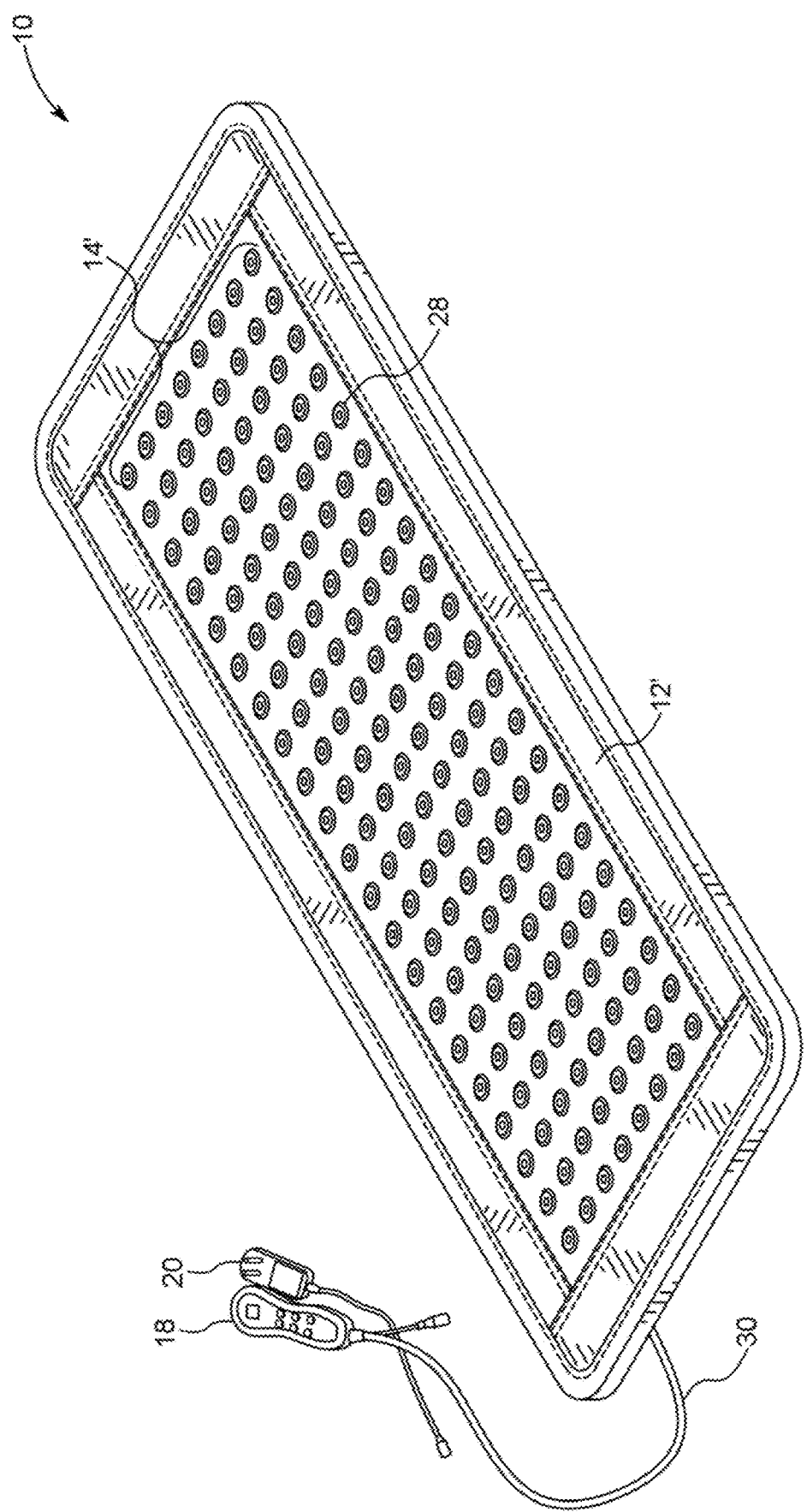
FIG. 2 is a perspective view of a second embodiment of a wavelength specific photo-modulation dermal treatment device housed in an elongated foldable and rollable mat including a remote controller and a power supply.
Figure 3:
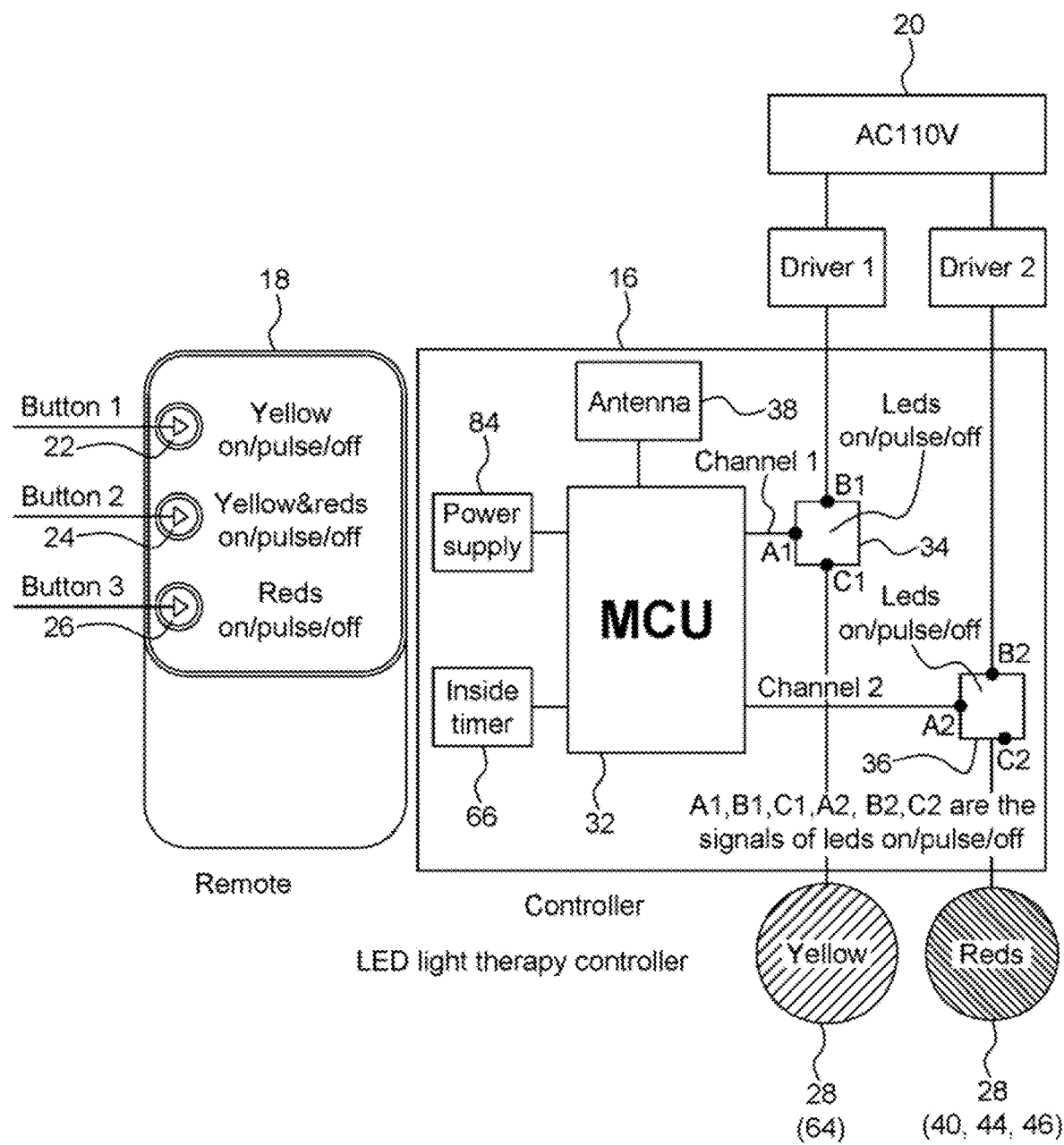
FIG. 3 is a schematic representation of the control system at a remote controller of an example embodiment.

As best seen in FIG. 2, the remote control has only three buttons, first button 22, second button 24 and third button 26. The first button 22 only controls operation of the yellow LED's 64 in either a first constant on, or second pulse mode, or off mode. The pulse mode preferably includes a duty cycle of 62.5% wherein the light emitting diodes are on for 250 m sec and off for 150 m sec. Similarly, the second button 24 operates in a first or second mode in which all of the LED's 40, 44, 46 and 64 (yellow and all reds) are either operating in a constant ON or pulse mode following the same duty cycle. The third button 26 cycles only the red LED's (40, 44, 46) though a constant ON first mode, and a pulsed second mode employing the duty cycle. The controller 16 includes a timer, 66 which limits the duration of treatment regardless of the mode or colors used to a maximum of approximately 20 minutes.

As stated above the specific wavelengths and modes chosen for treatment are directed to different modalities and maladies of the human body. Infrared treatment by 850 nm near-infrared LED's 46 result in deeper penetration to the body of the electromagnet radiation. Yellow LED's 64 at 590 nm are used to treat sensitive skin which has been sun damaged. Short red LED's 40 and red LED's 44 having wavelengths of approximately 630 and 660 nm respectively, are used for anti-aging treatments and pain relief and wound care. As stated above, yellow lights should only be utilized during the daylight hours, as it may disrupt sleep patterns.

Although red light therapy has been around for over 40 years, the Applicant's herein have discovered that the specific red-light wavelengths selected for the LED's 40, 44, and 46 effect bodily cells in a biochemical level by increasing mitochondrial function when red light wavelengths penetrate 8 to 10 millimeters into the skin. Red light therapy is believed to decrease skin inflammation, smooth skin tone, repair sun damage, fade scars and stretch marks, and build collagen in the skin which reduces wrinkles. Wound healing is also improved. Red light therapy also enhances lymphatic system flow to improve the body's detoxification abilities by increasing blood flow. Benefits include enhanced blood circulation, anti-inflammatory effects, increase muscle recovery, increase collagen production, radiant skin, reducing scars, wrinkles and fine lines, speeds wound healing, enhances fertility, increases testosterone and decreases pain. The near-infrared LED's 46 penetrate deeper through the dermal layer into bone and for open wounds, the selected way of lights of 630 nm and 660 nm accelerate healing. Near-infrared light radiation is used to treat a variety of injuries, especially infected, and blood restricted bones. Near-infrared light penetrates more deeply than ultraviolet or visible light and is benign to living tissue. Near-infrared light generates virtually no heat thereby avoiding thermal injury and is well tolerated by biological tissues having no known detrimental effects. Near-infrared light operates by activating color sensitive chemicals supplied to tissues, stimulating the process and the cell's mitochondria. Light wavelengths from 680 nm to 880 nm have been found to travel through skin and muscle tissue, to promote tissue and deep wound healing. Light penetration depends on power and wavelength, with higher frequency wavelength, shorter LED's more likely to penetrate further. The basic premise is that long wavelength light stimulates cellular energy, metabolism and energy production. The three major photo acceptor molecules in human tissue are known to absorb light in the near-infrared range: hemoglobin, myoglobin and cytochrome co-oxidase. Of these three, C oxidase has been associated with energy production. Wavelengths centered around 810 nm may be disruptive to cellular activity.

Yellow light therapy, also sometimes referred to as amber light therapy is concentrated at 580 nm for the LED 64. Irradiation at this wavelength creates primary cellular movement at the top layer of the dermis and although having shallow skin penetration is effective for the treatment of skin issues involved with redness such as spider veins and sun damaged tissue. Yellow light therapy is a drug free alternative treatment for skin redness and flushing, skin irritation, rosacea, ultraviolet radiation damage, reducing the appearance of tiny blood vessels on the nose/face, flushes from the skin, blood flow and increase cellular growth. Yellow light therapy effectively reduces the symptoms of redness among many rosacea sufferers, because the blood vessels can reduce in size following the treatment. As a result, those blood vessels and their red color become less visible. This action makes LED yellow light therapy sessions extremely safe and appropriate for all skin types including those who are sensitive and reactive. Yellow light therapy also stimulates the production of red blood cells, which plays a vital role in skin healing and skin rejuvenation. Yellow light therapy helps to give the look of being healthier overall. The selective shallow penetration of yellow light therapy exposes cells to light that are primarily visible. Thus, the greatest impact on the skin occurs where it can actually be seen as it is absorbed and uses a part of the natural healing process clearing rosacea symptoms without causing irritation or any other unwanted skin effects.

Use of the second, pulsing mode promotes rapid healing of body tissue. When photo therapy is given in a continuous burst, the cells are sedated, and pain is reduced. When a single frequency of light is absorbed by a cell, the cell is stimulated to start producing more protein than it normally does. As a result, the cells heal more quickly. Even after exposure to the pulsating LED light, once the source is removed, the cells continue healing. Operating the LED's in a continuous mode has a reverse effect that kills and dulls pain, reduces inflammation and allows muscle tissues to relax.

Figure 5:
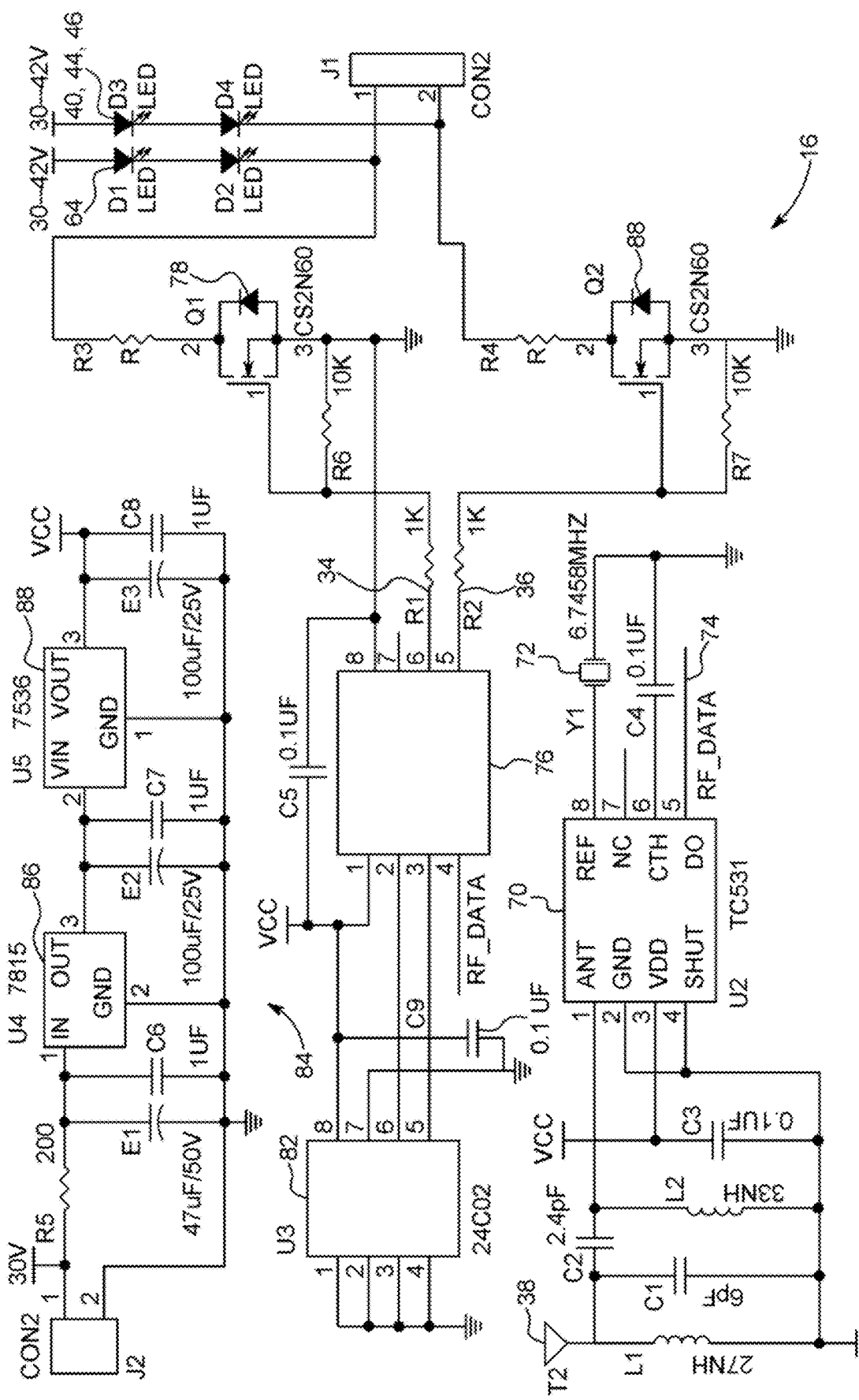
FIG. 5 is a schematic diagram of the control system for the treatment device.

FIG. 5 is an electronic schematic diagram of the individual circuit components of the controller 16. In its preferred embodiment, the controller 16 includes the receiving antenna 38 for receiving signals from the remote control 18.

The antenna is tuned through inductors L1, L2 as well as capacitors C1 through C3 providing an input to antenna pin 1 on integrated circuit, U2, a large integrated circuit receiver 70 (Part No. TC 531). The receiver 70 accepts a clock signal from a clock 72 so as to provide radio frequency output data 74 on pin 5. That data is received by large scale integrated circuit U2, a conventional micro-controller 76 at pin 4. The micro-controller has the first channel driver signal 34 at pin 6 and the second channel driver signal 36 at pin 5. Those channels drive a first field effect transistor (FET) 78 and a second field effect transistor (FET) 80 which respectively drive the yellow LED's 64, and red LED's 40, 44, 46. The micro-controller 76 draws instructions and methods steps from a large-scale integrated circuit U3, an erasable electronic programmable read-only memory (EEPROM, Part No. 24c02) 82. The EEPROM instructions received on pin 3 of the micro-controller 76. The controller 16 is provided with an internal power supply generally indicated by the reference numeral 84 consisting of a conventional voltage regulator 86 (U4 Page No. 7815) and a low power drop out voltage regulator 88 (U5, Page No. 7536) to provide Vcc for large scale integrated circuits U1 through U3.

Figure 6:
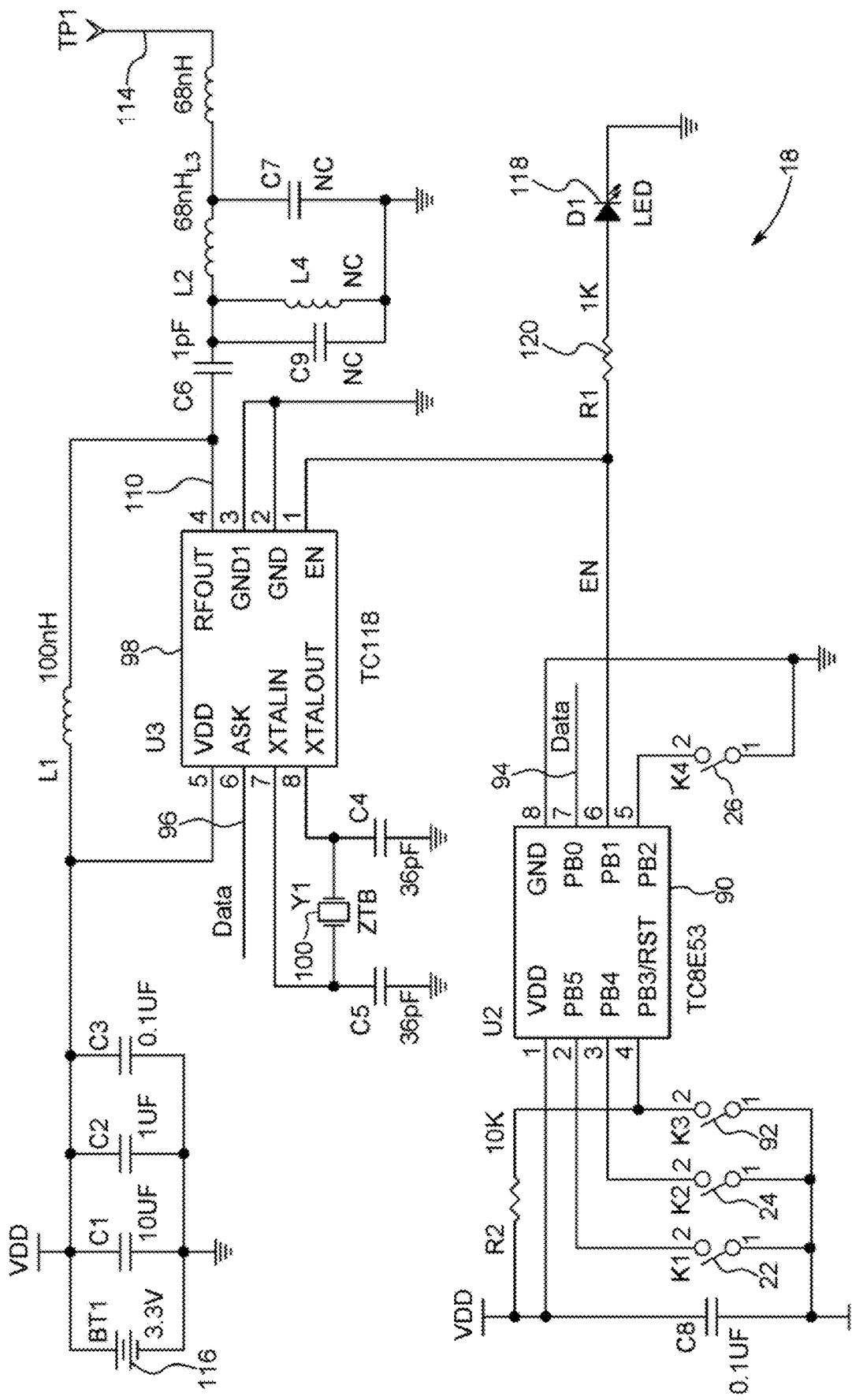
FIG. 6 is an electronic schematic for a remote controller for the treatment device.

FIG. 6 is an electronic schematic diagram for the remote control 18 consisting of a large-scale integrated circuit, U2 (Page No. TC 8853) multiplexer 90 operatively connected to the first, second and third buttons 22, 24, and 26 at pins 2, 3 and 5 of the multiplexer. Pin 4 is connected to a corrected reset switch 92 not shown on the remote control 18. Data out 94 from the multiplexer as is provided on pin 7 to data in 96 on pin 6 of a large-scale integrated circuit U3 (Page No. TC115) use of 3 radio frequency transmitter 98. The transmitter is driven by a transmitter clock 100 connected to pins 7 and 8 so that transmitter 87 can provide a radio frequency output 110 at pin 4. The radio frequency output 110 is tuned by inductors L1-L4 and capacitors C1-C7 to broadcast the radio frequency output 110 on transmitting antenna 114. A 3.3 volt DC power supply 116 supplies DC voltage to the radio frequency transmitter 98 and multiplexer 90. The DC supply voltage may be in the form of two AA batteries. Finally, multiplexer 90 drives a display LED 118 through a resistor 120 to provide illumination to the first, second and third buttons 22, 24, 26 providing visual feedback to the user that a button depression has been registered.

Figure 7:
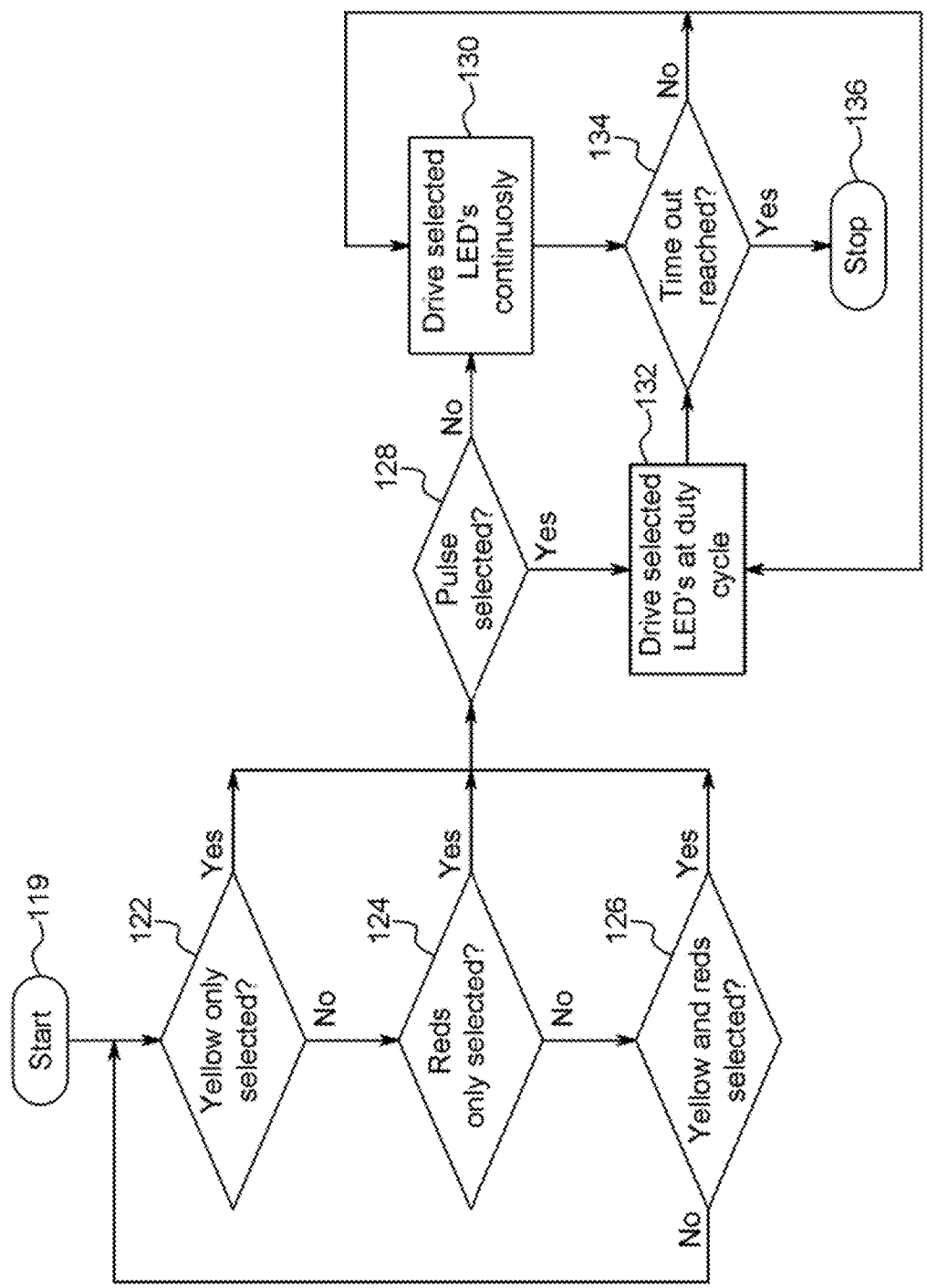
FIG. 7 is a logical flow diagram of the methods steps stored in a memory of the control system

FIG. 7 is a logic flow diagram for the program implemented in the micro controller 76 and stored in the EEPROM 82. In a first user step 119, the user selects one of the buttons 22, 24 and 26. The program determines at step 122, 124 and 126 which button has been selected. If the button is released, and pushed again, the pulse mode (Mode 2) will be selected at step 128. If the button is not pushed again, the constant on mode (Mode 1) will be selected. If mode 1 is selected the selected LED's will be driven continuously at step 130. If mode 2 is selected, the selected LED's will driven at the duty cycle in step 132. In either case, once the pre-program time out is reached in step 134 and the program stops at reference 136. In an alternative embodiment, if any button is pressed for a third time in any mode, before time out, the process stops.

Those of ordinary skill in the art will conceive of other alternate embodiments upon reviewing this disclosure. Thus, the invention is not to be limited to the above description but is to be determined in scope by the claims which follow.

The invention claimed is:

1. A photo-modulation dermal treatment device comprising:

a plurality of narrow bandwidth light emitting devices being arranged in rows and columns and comprising a first subset of light emitting devices and a second subset of light emitting devices, the first subset of light emitting devices being configured to emit red light and infrared light, the second subset of light emitting devices being configured to emit yellow light, wherein a total number of the rows is the same as a total number of the columns, wherein a first subset of the rows comprises the first subset of light emitting devices and none of the second subset of light emitting devices, and a second subset of the rows comprises the second subset of light emitting devices and none of the first subset of light emitting devices, wherein the rows include at least twice as many of the first subset of the rows as the second subset of the rows, wherein the first subset of light emitting devices are configured to emit a plurality of different wavelengths of the red light and a common wavelength of the infrared light, and the second subset of light emitting devices are configured to emit a common wavelength of the yellow light;

a controller configured to operate the plurality of narrow bandwidth light emitting devices in a first mode, a second mode, and a third mode, wherein in the first mode, the controller is configured to activate the first subset of light emitting devices to emit the red light and the infrared light and deactivate the second subset of light emitting devices, wherein in the second mode, the controller is configured to deactivate the first subset of light emitting devices and activate the second subset of light emitting devices to emit the yellow light, wherein in the third mode, the controller is configured to activate the first subset of light emitting devices to emit the red light and the infrared light and activate the second subset of light emitting devices to emit the yellow light; and a user interface configured to permit a user to select the first mode, the second mode, or the third mode in which to operate the plurality of narrow bandwidth light emitting devices for treatment of skin tissue, wherein the controller is configured to operate the plurality of narrow bandwidth light emitting devices in a pulse mode in which:

in the first mode and the third mode, the controller is configured to at least twice activate the first subset of light emitting devices to emit the red light and the infrared light for a first duration and then deactivate the first subset of light emitting devices for a second duration, the first duration being 250 ms, the second duration being shorter than the first duration, and in the second mode and the third mode, the controller is configured to at least twice activate the second subset of light emitting devices to emit the yellow light for the first duration and then deactivate the second subset of light emitting devices for the second duration, and wherein the controller is configured to:

monitor a duration of treatment by the plurality of narrow bandwidth light emitting devices, and deactivate the plurality of narrow bandwidth light emitting devices responsive to the duration of treatment satisfying a duration threshold.

2. The photo-modulation dermal treatment device of claim 1, wherein the plurality of narrow bandwidth light emitting devices comprises a plurality of light emitting diodes.

3. The photo-modulation dermal treatment device of claim 1, wherein in the pulse mode and the third mode, the controller is configured to at least twice:
- simultaneously activate the first subset of light emitting devices to emit the red light and the infrared light for the first duration and activate the second subset of light emitting devices to emit the yellow light for the first duration, and
- then simultaneously deactivate the first subset of light emitting devices for the second duration and deactivate the second subset of light emitting devices for the second duration.

4. The photo-modulation dermal treatment device of claim 1, wherein the user interface is configured to permit the user to select the pulse mode.

5. The photo-modulation dermal treatment device of claim 1, wherein the red light has wavelengths of 630 nm and 660 nm, the infrared light has a wavelength of 850 nm, and the yellow light has a wavelength of 580 nm.

6. A photo-therapeutic treatment method for treating skin tissue, the photo-therapeutic treatment method comprising:
- receiving, via a user interface, a first user input to select a first mode;
- in response to receiving the first user input, activating a first subset of light emitting devices of a plurality of narrow bandwidth light emitting devices to emit red light and infrared light and not activating a second subset of light emitting devices of the plurality of narrow bandwidth light emitting devices, the plurality of narrow bandwidth light emitting devices being arranged in rows and columns,
- wherein a total number of the rows is the same as a total number of the columns,
- wherein a first subset of the rows comprises the first subset of light emitting devices and none of the second subset of light emitting devices, and a second subset of the rows comprises the second subset of light emitting devices and none of the first subset of light emitting devices,
- wherein the rows include more of the first subset of the rows than the second subset of the rows;
- receiving, via the user interface, a second user input to select a second mode;
- in response to receiving the second user input, activating the second subset of light emitting devices to emit yellow light and not activating the first subset of light emitting devices,
- wherein the first subset of light emitting devices emit a plurality of different wavelengths of the red light and a common wavelength of the infrared light, and the second subset of light emitting devices emit a common wavelength of the yellow light;
- receiving, via the user interface, a third user input to select a third mode;
- in response to receiving the third user input, activating the first subset of light emitting devices to emit the red light and the infrared light and activating the second subset of light emitting devices to emit the yellow light;
- receiving, via the user interface, a fourth user input to select a pulse mode;
- in response to receiving the fourth user input at least:
  - periodically activating the first subset of light emitting devices to emit the red light and the infrared light for a first duration and then deactivating the first subset of light emitting devices for a second duration, or
  - periodically activating the second subset of light emitting devices to emit the yellow light for the first duration and then deactivating the second subset of light emitting devices for the second duration;
- monitoring a duration of treatment by the plurality of narrow bandwidth light emitting devices; and
- deactivating the plurality of narrow bandwidth light emitting devices responsive to the duration of treatment satisfying a duration threshold,
- wherein the first duration is 250 ms, and the second duration is shorter than the first duration.

7. The photo-therapeutic treatment method of claim 6, wherein the plurality of narrow bandwidth light emitting devices comprises a plurality of light emitting diodes.

8. The photo-therapeutic treatment method of claim 6, wherein said periodically activating the first subset of light emitting devices and then deactivating the first subset of light emitting devices is performed in response to receiving the fourth user input.

9. The photo-therapeutic treatment method of claim 8, wherein said periodically activating the second subset of light emitting devices and then deactivating the second subset of light emitting devices is performed in response to receiving the fourth user input.

10. The photo-therapeutic treatment method of claim 6, wherein said periodically activating the second subset of light emitting devices and then deactivating the second subset of light emitting devices is performed in response to receiving the fourth user input.

11. The photo-therapeutic treatment method of claim 6, wherein the red light has wavelengths of 630 nm and 660 nm, the infrared light has a wavelength of 850 nm, and the yellow light has a wavelength of 580 nm.

* * * * *